(12) United States Patent
Young et al.

(10) Patent No.: US 9,173,672 B2
(45) Date of Patent: Nov. 3, 2015

(54) ULTRASONIC SURGICAL TOOL

(75) Inventors: Michael John Radley Young, Asburton (GB); Stephen Michael Radley Young, Ashburton (GB)

(73) Assignee: SRA DEVELOPMENTS LIMITED, Ashburton, South Devon (GB)

( * ) Notice: Subject to any disclaimer, the term of this patent is extended or adjusted under 35 U.S.C. 154(b) by 1125 days.

(21) Appl. No.: 12/301,384

(22) PCT Filed: May 25, 2007

(86) PCT No.: PCT/GB2007/001968
§ 371 (c)(1),
(2), (4) Date: May 13, 2009

(87) PCT Pub. No.: WO2007/138295
PCT Pub. Date: Dec. 6, 2007

(65) Prior Publication Data
US 2010/0004667 A1    Jan. 7, 2010

(30) Foreign Application Priority Data

May 31, 2006    (GB) .................................. 0610715.5

(51) Int. Cl.
*A61B 17/32*  (2006.01)
*A61B 17/00*  (2006.01)

(52) U.S. Cl.
CPC . *A61B 17/320068* (2013.01); *A61B 17/320092* (2013.01); *A61B 2017/00017* (2013.01); *A61B 2017/00137* (2013.01)

(58) Field of Classification Search
CPC ........... A61B 2018/00601; A61B 2018/00577; A61B 2018/1412; A61B 18/1402; A61B 17/320068; A61B 17/320092; A61B 17/00017; A61B 2017/00137; A61N 7/00; A61N 2007/0078

USPC .................................................. 606/169, 37
See application file for complete search history.

(56) References Cited

U.S. PATENT DOCUMENTS 2,528,941 A    11/1950    Bassett et al.
3,565,062 A     2/1971    Kuris
(Continued)

FOREIGN PATENT DOCUMENTS

EP    0 619 993 A1    10/1994
EP    0 646 435 A1     4/1995
(Continued)

OTHER PUBLICATIONS

PCT International Search Report for PCT/GB2007/003560 filed Sep. 18, 2007, dated Jan. 3, 2008.
(Continued)

*Primary Examiner* — Thomas McEvoy
*Assistant Examiner* — Julie A Szpira
(74) *Attorney, Agent, or Firm* — Heslin Rothenberg Farley & Mesiti P.C.

(57) ABSTRACT

At the surgical tool's proximal end, there is a first means (3) to generate ultrasonic vibration in a torsional shear mode. There is also a second means (2) to generate ultrasonic vibration in a longitudinal compression mode. A wave guide (4) is operatively connected to both generating means and extending therefrom by a distance of $n\lambda/2$ to a distal end provided with cutting and/or coagulating means. The ratio of the wavelengths of the longitudinal compression wave and the torsional shear wave, $\lambda c : \lambda \tau$, is an odd number. Preferably $\lambda c = N^x \lambda \tau$ (where N is an odd integral number and x is an integer). Delicate shear motion of the torsional ultrasonic vibrational mode is combined with the more vigorous excitation of the longitudinal compression wave ultrasonic vibration.

15 Claims, 1 Drawing Sheet

(56) References Cited

U.S. PATENT DOCUMENTS

Figure 1:
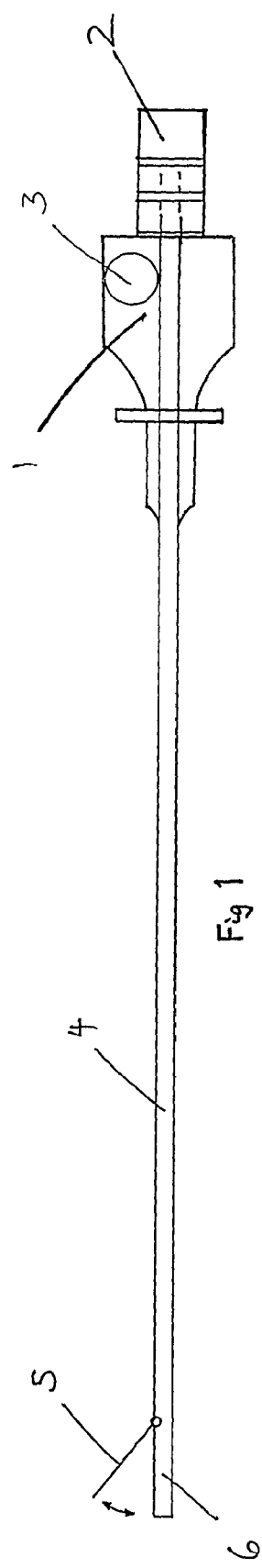

| | | | |
|---|---|---|---|
| 3,657,056 A | 4/1972 | Garvey et al. | |
| 3,792,701 A | 2/1974 | Kloz et al. | |
| 3,861,391 A | 1/1975 | Antonevich et al. | |
| 4,144,646 A | 3/1979 | Takemoto et al. | |
| 4,188,952 A | 2/1980 | Loschilov et al. | |
| 4,248,232 A | 2/1981 | Engelbrecht et al. | |
| 4,832,683 A | 5/1989 | Idemoto et al. | |
| 5,019,083 A | 5/1991 | Klapper et al. | |
| 5,151,099 A | 9/1992 | Young et al. | |
| 5,167,619 A | 12/1992 | Wuchinich | |
| 5,322,055 A | 6/1994 | Davison et al. | |
| 5,324,297 A | 6/1994 | Hood et al. | |
| 5,324,299 A | 6/1994 | Davison et al. | |
| 5,330,481 A | 7/1994 | Hood et al. | |
| 5,413,107 A | 5/1995 | Oakley et al. | |
| 5,520,678 A | 5/1996 | Heckele et al. | |
| 5,527,273 A * | 6/1996 | Manna et al. | 604/22 |
| 5,549,544 A | 8/1996 | Young et al. | |
| 5,656,015 A | 8/1997 | Young | |
| 5,695,510 A | 12/1997 | Hood | |
| 5,749,877 A | 5/1998 | Young | |
| 5,873,873 A | 2/1999 | Smith et al. | |
| 5,885,301 A | 3/1999 | Young | |
| 5,935,143 A | 8/1999 | Hood | |
| 6,004,335 A | 12/1999 | Vaitekunas et al. | |
| 6,056,735 A | 5/2000 | Okada et al. | |
| 6,129,735 A | 10/2000 | Okada et al. | |
| 6,283,981 B1 | 9/2001 | Beaupre | |
| 6,425,906 B1 | 7/2002 | Young et al. | |
| 6,790,216 B1 * | 9/2004 | Ishikawa | 606/169 |
| 6,971,994 B1 | 12/2005 | Young et al. | |
| 2002/0091404 A1 * | 7/2002 | Beaupre | 606/169 |
| 2002/0099400 A1 | 7/2002 | Wolf et al. | |
| 2003/0045887 A1 | 3/2003 | Sakurai et al. | |
| 2004/0044356 A1 | 3/2004 | Young et al. | |
| 2005/0021065 A1 * | 1/2005 | Yamada et al. | 606/169 |
| 2005/0177184 A1 | 8/2005 | Easley | |
| 2006/0036180 A1 * | 2/2006 | Boukhny et al. | 600/471 |
| 2006/0058825 A1 * | 3/2006 | Ogura et al. | 606/169 |

FOREIGN PATENT DOCUMENTS

| | | |
|---|---|---|
| EP | 0 970 659 A1 | 1/2000 |
| EP | 0970660 A1 | 1/2000 |
| EP | 1138264 A1 | 10/2001 |
| EP | 1 229 515 A2 | 8/2002 |
| EP | 1 625 836 | 2/2006 |
| EP | 1 693 027 A | 8/2006 |
| GB | 2333709 | 8/1999 |
| GB | 2333709 A | 8/1999 |
| GB | 2 365 775 A | 2/2002 |
| GB | 2425480 A | 11/2006 |
| JP | 2003-116863 | 4/2003 |
| JP | 2005-040222 | 2/2005 |
| JP | H11-113920 | 4/2011 |
| SU | 1388002 A1 | 4/1988 |
| WO | WO 99/35982 | 7/1999 |
| WO | WO 99/52489 | 10/1999 |
| WO | WO 01/21079 A1 | 3/2001 |
| WO | WO 01/52782 | 7/2001 |
| WO | WO 02/38057 | 5/2002 |
| WO | WO 03/047769 | 6/2003 |
| WO | WO 03/082132 A1 | 10/2003 |
| WO | WO 03082133 | 10/2003 |
| WO | WO 2005/084553 | 9/2005 |
| WO | WO 2006/008502 | 1/2006 |
| WO | WO 2006/059120 | 6/2006 |
| WO | WO 2006/092576 | 9/2006 |
| WO | WO 2007/138295 | 12/2007 |
| WO | WO 2008/065323 | 6/2008 |

OTHER PUBLICATIONS

GB Search Report for GB 0718476.5 dated Nov. 29, 2007.
PCT International Preliminary Report on Patentability for PCT/GB2007/003560 filed Sep. 18, 2007, dated Mar. 24, 2009.
PCT International Preliminary Report on Patentability for PCT/GB2006/000697 filed Feb. 28, 2006, dated Sep. 11, 2007.
International Search Report for PCT/GB2006/000697 dated May 3, 2006.
GB Search Report dated Jun. 27, 2006 for GB0504321.1.
PCT Written Opinion of the International Searching Authority for Appln. No. PCT/GB2007/001968 filed May 25, 2007, European Patent Office.
PCT International Search Report dated Sep. 12, 2007 for Appln. No. PCT/GB2007/001968 filed May 25, 2007.

* cited by examiner

ULTRASONIC SURGICAL TOOL

The present application is a national stage entry of PCT/GB07/01968, filed May 25, 2007, which claims priority to UK application 0610715.5 filed May 31, 2006.

The present invention relates to an ultrasonic surgical tool for cutting and/or ablating soft material such as flesh or blood vessels. More particularly, but not exclusively, it relates to a tool for haemostatic cutting of soft material, particularly in a laparoscopic surgical system.

It has long been known to cut and/or cauterise tissue by means of ultrasonic tools which vibrate in a longitudinal mode. These have disadvantages in that prolonged use in such mode can affect tissue in a region extending beyond the end of the tool being used. First reason, tools utilising ultrasonic vibration in a torsional mode have been developed, as described in our Patent No. GB2333709-B. Use of such torsionally vibratable devices can direct the power very accurately to a specific point. However, in some cases, where the tissue to be addressed is large, it will be advantageous to increase the size of the jaws at the distal end of the wave guide. In this case, the comparatively short wavelength of the torsional mode of vibrations can be its advantage.

It would be advantageous if the benefits of the delicate shear motion of torsional ultrasonic vibrational mode could be combined with the more vigorous excitation of the a) longitudinal compression wave ultrasonic vibration.

Single frequency activation provides for a distal blade whose effective length is related to the quarter wavelength at the operating frequency. The higher the frequency, the shorter the active length of blade. Thus it follows that, for a titanium waveguide operating at 50 kHz in a torsional mode the blade length would be limited to 15.5 mm which is a quarter wavelength defining the first distal mode position. The corresponding blade length for a compression wave at 50 kHz would be 24.5 mm.

Each vibration mode has its own advantages, but, in any case, it is inappropriate to operate the tool with both modes in use simultaneously.

It is therefore an object of the present invention to provide a tool in which a waveguide may be operated intermittently at two different alternative frequencies, one stimulating in a torsional mode and the other in a longitudinal mode. In order to produce a practical system it must, of course, be possible to isolate the waveguide at well defined nodal planes. This can only be achieved by ensuring that there is coincidence of displacement nodes in the two operating modes.

According to the first aspect of the present invention, there is provided a surgical tool comprising at a proximal end, a first means to generate ultrasonic vibration in a torsional shear mode and a second means to generate ultrasonic vibration in a longitudinal compression mode, a wave guide operatively connected to both said generating means and extending therefrom by a distance of $n\lambda/2$ to a distal end provided with cutting and/or coagulating means, wherein the ratio of the wavelengths of the longitudinal compression wave and the torsional sheer wave, $\lambda_C:\lambda_T$, is an odd number.

The ratio is preferably $\lambda_C = N^x \lambda_T$ where N is an odd integral number and x is an integer Preferably N is 3 and x is 1, in which case the ratio is 3:1.

In any event, the longer wavelength compression wave should have nodes which coincide with at least some of the nodes of the shorter wavelength torsional wave.

In this case the waveguide may be supported and/or insulated at these common nodal points.

Advantageously, the tool is operable for part of the time in longitudinal vibration mode and for part of the time in torsional vibration mode.

The vibration mode in operation at any one time may be selected by the surgeon or user of the apparatus.

Alternatively, the tool may be adapted to alternate between the vibrational modes.

The vibrational modes may alternate at a predetermined frequency.

The predetermined frequency may be between 0.5 and 5 kHz, preferably in the region of 2 kHz.

Figure 2:
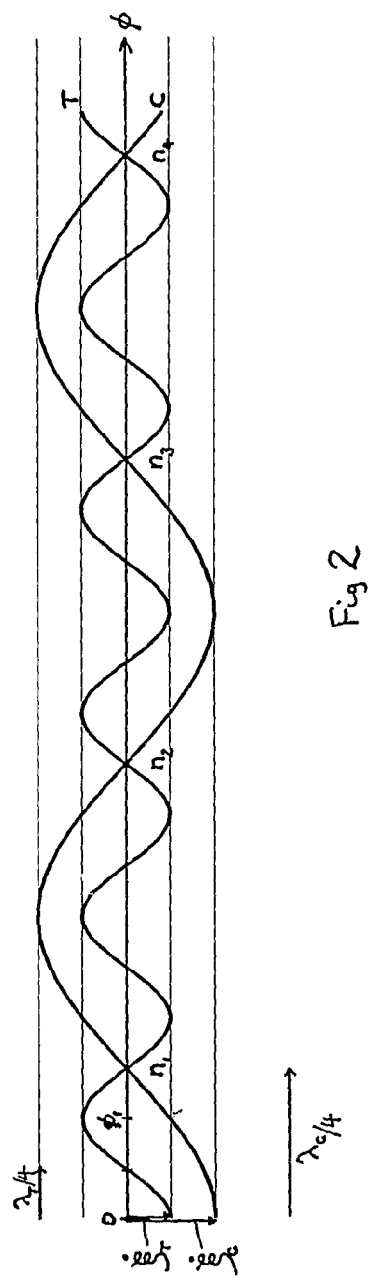

An embodiment of the present invention will now be more particularly described by way of example and with reference to the accompanying drawings, in which:

FIG. 1 illustrates schematically an ultrasonically powered surgical tool embodying the invention; and FIG. 2 shows the wave forms generatable along the tool.

Referring to the drawings, FIG. 1 shows a surgical tool, for use primarily in laparoscopic procedures.

The surgical tool comprises, at its proximal end, a conversion horn 1 to which are connected two piezoceramic transducer ultrasonic drivers, a first driver 2 acting in a longitudinal direction to generate a longitudinal compression wave of wavelength $\lambda_c$ and a second driver 3 acting tangentially to generate a torsional wave of wavelength $\lambda_T$.

In operation, either of these waveforms is transmitted along the waveguide 4, which has a length of $n\lambda/2$ for both $\lambda_c$ and $\lambda_T$.

At the distal end of the waveguide 4 is a hinged jaw arrangement with one vibratable arm of the jaw formed by the waveguide and the other non-vibratable passive arms 5 of the jaw hinged to a shroud (not shown) of the waveguide and operable to move into and out of engagement with the vibratable arm of the jaw.

Referring now to FIG. 2, which shows exemplary waveforms for both modes along the length of the tool, it can be seen that the power delivered at the distal end of jaw is given by the following.

Torsional wave power $P_T$ is defined by:

$$P_T = 1/2 \, W \int_0^{\phi_1} (\xi_{T0} \cos\phi)^2 \cdot d\phi$$

where $\xi_{T0}$ is the particle velocity at the distal tip; $\phi$ represents the phase angle from the distal end; and W is the tissue impedance. W equals $\rho.c$ where $\rho$ is the density of the tissue and c is the sound velocity in the tissue. Note: $\phi=0°$ at the distal tip and $\phi_1 = 180°$ at the jaw pivot.

Compression wave power $P_C$ is defined by:

$$P_C = 1/2 \, F \int_0^{\phi_1} \xi_{C0} \cos\phi \cdot d\phi$$

Where $\mu_{C0}$ is the particle velocity for the compression wave and F is the mean frictional force at the blade/tissue interface. F equals $p.a.\mu$ where p is the pressure applied to the tissue, a is the contact area between blade and tissue and $\mu$ is the friction coefficient at the friction interface.

Each waveform is applied in turn, preferably at a wave switching frequency of about 2 kHz. The power delivery is the sum of the products $P_T.T_1$ and $P_C.T_2$, where $T_1$ and $T_2$ are the respective torsional and compression wave intervals. However, the intervals could be variable according to a predetermined program depending on the interval being addressed.

Use of the tool embodying the invention will permit action to be taken utilising the highly specific torsional mode techniques on material larger than would normally be the case.

The invention claimed is:

1. A surgical tool comprising at a proximal end, a first means to generate ultrasonic vibration in a torsional shear mode having a wavelength $\lambda_T$ and a second means to generate ultrasonic vibration in a longitudinal compression mode having a wavelength $\lambda_C$, a wave guide operatively connected to said first and to said second generating means and extending therefrom by a distance of $n\lambda/2$, where n is an integer and $\lambda$ is a wavelength for both $\lambda=\lambda_C$ and $\lambda=\lambda_T$, to a distal end provided with cutting and/or coagulating means, wherein wavelengths of the longitudinal compression wave ($\lambda_C$) and the torsional shear wave ($\lambda_T$) propagating through the waveguide are different, and the ratio $\lambda_C:\lambda_T$ of the wavelengths of the longitudinal compression wave ($\lambda_C$) and the torsional shear wave ($\lambda_T$), as the longitudinal compression wave and the torsional shear wave propagate through the wave guide, is an odd number.

2. A tool as claimed in claim 1, wherein the ratio $\lambda_C:\lambda_T=N^x$, where N is an odd, positive integer and x is a positive integer.

3. A tool as claimed in claim 2, wherein N is 3 and x is 1, in which case the ratio $\lambda_C:\lambda_T$ is 3:1.

4. A tool as claimed in claim 1, wherein the wavelength of the longitudinal compression wave $\lambda_C$ is longer than the wavelength of the torsional shear wave $\lambda_T$.

5. A tool as claimed in claim 4, wherein the longitudinal compression wave in the wave guide has nodes which coincide with at least some of nodes of the torsional shear wave in the wave guide.

6. A tool as claimed in claim 5, wherein the waveguide is supported and/or insulated at nodal points common to both the longitudinal compression wave and the torsional shear wave.

7. A tool as claimed in claim 1, wherein the longitudinal compression wave in the wave guide has nodes which coincide with at least some of nodes of the torsional shear wave in the wave guide.

8. A tool as claimed in claim 7, wherein the waveguide is supported and/or insulated at nodal points common to both the longitudinal compression wave and the torsional shear wave.

9. A tool as claimed in claim 1, wherein the tool is operable for part of the time in longitudinal compression vibration mode and for part of the time in torsional shear vibration mode.

10. A tool as claimed in claim 9, wherein vibration mode in operation at any one time is selected by a surgeon or user of the apparatus.

11. A tool as claimed in claim 9, wherein the tool is adapted to alternate between the longitudinal compression vibrational mode and the torsional shear mode.

12. A tool as claimed in claim 9, wherein the tool is adapted to alternate between vibrational modes at a predetermined switching frequency.

13. A tool as claimed in claim 12, wherein the predetermined switching frequency is between 0.5 kHz and 5 kHz.

14. A tool as claimed in claim 12, wherein the predetermined switching frequency is about 2 kHz.

15. A tool as claimed in claim 1, further comprising, at a distal end of the wave guide, a hinged jaw arrangement with one vibratable arm of the jaw formed by the wave guide and an other non-vibratable passive arm of the jaw hinged to a shroud of the wave guide and operable to move into and out of engagement with the vibratable arm of the jaw.

* * * * *

UNITED STATES PATENT AND TRADEMARK OFFICE
CERTIFICATE OF CORRECTION

PATENT NO. : 9,173,672 B2  Page 1 of 1
APPLICATION NO. : 12/301384
DATED : November 3, 2015
INVENTOR(S) : Young et al.

It is certified that error appears in the above-identified patent and that said Letters Patent is hereby corrected as shown below:

Column 2, Line 59: Specification, Delete "Where μco" and insert -- Where ξco --

Column 4, Line 27: Claims, Claim 14, Delete "claim 12" and insert -- claim 13 --

Signed and Sealed this
Eighth Day of March, 2016

Michelle K. Lee
*Director of the United States Patent and Trademark Office*